United States Patent [19]
Bentvelsen et al.

[11] Patent Number: 5,585,540
[45] Date of Patent: Dec. 17, 1996

[54] FRAGARIA PLANTS AND SEEDS

[75] Inventors: Gerardus C. M. Bentvelsen, Grootebrock; Willem Sterk, Enkhuizen, both of Netherlands

[73] Assignee: Sandoz Ltd., Basle, Switzerland

[21] Appl. No.: 437,828

[22] Filed: May 9, 1995

Related U.S. Application Data

[63] Continuation of Ser. No. 211,372, Mar. 31, 1994, abandoned.

[51] Int. Cl.$^6$ ............... A01H 5/00; A01H 1/00; A01H 5/08; A01H 5/10

[52] U.S. Cl. ................ 800/200; 800/DIG. 11; PLT./48.1; 47/58

[58] Field of Search .................. 800/200, 208, 800/DIG. 11; PLT./48.1; 47/58.03, 58

[56] References Cited

PUBLICATIONS

Pan–American Seed. (1990) "*SweetHeart; Introducing a new strawberry plant from seed*", Catalog Sheet.
Scott et al. (1975) *Strawberries* In Advances in Fruit Breeding, edited by Jules Janick et al., Purdue University Press, pp. 71–97.
Poehlman John, Milton. (1987) *Breeding Field Crops*. AVI Publishing Company, Inc. pp. 237–254.

*Primary Examiner*—Gary Benzion
*Attorney, Agent, or Firm*—Lynn Marcus-Wyner

[57] ABSTRACT

Polyploid Fragaria plants propagatable from seed wherein substantially each plant is capable of a fruit productivity within its first year, F1 hybrid Fragaria plants, methods for producing F1 hybrid Fragaria plants, F1 hybrid Fragaria seed, and Fragaria berries thereof.

19 Claims, 4 Drawing Sheets

FRAGARIA PLANTS AND SEEDS

This is a continuation of application Ser. No. 08/211,372 filed on Mar. 31, 1994, now abandoned.

The present invention relates to plants propagatable from seed and seeds therefor. In particular, the invention relates to polyploid Fragaria or strawberry plants which are propagatable from seed.

BACKGROUND

Polyploid Fragaria plants do not breed true and the genetics is very complex. The progeny of a vegetatively propagated variety fertilised with its own pollen are all different.

There have been some attempts to improve breeding strategies with a view to acquiring improved strawberry types however such strategies have met with limited or no success since problems associated with inbreeding depression have not been overcome.

Niemirowicz-Szycytt K.[(1989) Acta Horticulturae 265: 97–104] failed to control inbreeding depression within the inbreeding program employed and as a result did not obtain viable and suitably homogeneous (uniform) inbred lines capable of being used in inbreeding programs for obtaining agronomically attractive strawberry plants in commercial numbers.

Other workers have attempted to use alternative routes to obtain viable octoploid lines for use in strawberry breeding. Sayegh A. J. and Hemnarty M. J.[(1989) Acta Horticulturae 265: 129–135], attempted the production of haploids of commercial strawberry cultivars using androgenesis and intergeneric crosses followed by embryo rescue and culture. However, that approach was unsuccessful since the first essential step, that of obtaining haploids, was not realised and as a consequence the idea of doubling the haploid number to create octoploids and then selecting viable octoploid lines suitable for use in a breeding program could not be attempted.

A recurring problem associated with strawberry breeding programs as disclosed in the art is that inbred lines obtained through repeated selfing programs lack plant vigour and as a consequence are too weak to continue with further. Lack of plant vigour is generally evident at about the third or fourth or later generations.

In all cases, such programs have not been designed with a view to obtaining commercial quantities of F1 hybrids and seeds therefor. The goals of such breeding programs have been the acquisition of new breeding lines for use as basis for acquiring new varieties suitable for creating vegetatively propagated cultivars.

As a consequence of the difficulties associated with classical strawberry breeding techniques, breeders have faced an uphill task in improving their gene pool and each year breeders search for seedlings from within their breeding programs for plants which display desirable characteristics. Such Fragaria seedlings are propagated vegetatively by runners or by micro-propagation techniques for as long as necessary, however, seed from such seedling plants cannot generally be used for propagative purposes since plants resulting from such seed generally do not display phenotypic similarity in terms of commercially desirable characteristics in plant habit (Guttridge C. G. & Simpson D. W. Grower, Dec. 23,(1982) pp 28–29). Plants grown from seed harvested from vegetatively propagated cultivars typically display marked differences in appearance or plant habit. Such differences render them commercially and agronomically unacceptable.

Other disadvantages of supplying material grown via vegetative propagation and clonal propagation relate to the timing of release of such material to the grower. The propagator generally faces difficulties in timing and co-ordinating the release of sufficient numbers of strawberry plants to meet the requirements of the grower.

A further disadvantage of vegetatively propagated material is that there is a high risk of disease transmission in such material and when disease infestation is found, the use of chemicals to combat any disease infestation may become necessary which in turn not only leads to increased costs but also to potentially undesirable environmental effects. It follows from the above that if uniform inheritance of commercially desirable characteristics could be achieved in cultivated strawberry plants propagatable from seed such an achievement would mark a significant departure from current commercial strawberry production practices with the inbuilt limitations as outlined above, and pave the way for a highly attractive means of producing large numbers of strawberries in an efficient and cost effective manner.

Wild Fragaria species propagate from seed. However wild species generally produce small fruits and lack uniformity in appearance or plant habit.

Recently, there have been attempts to develop cultivated strawberry plants propagatable from seed, however, such attempts have met with limited success from a commercial point of view. One attempt at a seed propagatable strawberry, described as being commercially available from Pan American Seed is described in product brochures as seed propagatable, however, this variety suffers from the fact that up to only 75% of the plants grown from seed are capable of flowering and bearing fruit in their first season. The brochure does not disclose how said variety was obtained. Whilst a seed propagated strawberry which performed to such a specification may have satisfactory value to a gardener it would have dubious worth from an agronomical point of view for the commercial grower.

High ploidy levels, such as octoploidy in vegetatively propagated Fragaria, are generally associated with large berry size, while low ploidy levels such as diploidy are generally associated with smaller berry size. An example of a diploid species of strawberry, open pollinated $F.$ $vesca$, is grown commercially from seed and is suitable for use in fruit drink, preserves production and the like, since the fruits which this species produces are small and not generally attractive for consumption fresh. The strawberry fruit production market is generally dominated by polyploid Fragaria species which are propagated via vegetative propagation. Such types include inter alia the octoploid species $F.$ $x$ $ananassa$. It would be highly desirable if polyploid Fragaria plants displaying commercially important characteristics could be propagated from seed reliably and without the need for vegetative propagation techniques.

It results from the above that it is highly desirable to provide seed giving rise to polyploid Fragaria plants of which substantially each plant is capable of fruit productivity within its first year from sowing. The seeds should conveniently give rise to plants displaying similarity (i.e. substantial uniformity) in one or more commercially valuable traits and where desired display similarity in its overall plant habit.

Despite such clear advantages of polyploid Fragaria plants that are propagatable by seed and of which substantially each plant is capable of fruit productivity, such plants/ seed have not been provided for, the reasons being i.a. the complex genetics of the plants and the problems associated with the inbreeding depression typical for polyploid Fragaria plants.

It has now surprisingly been found that it is possible to apply inbreeding techniques suitable for diploids, such as the use of sib or half-sib families in inbreeding selection steps, to polyploid Fragaria plants and that when crossing a polyploid Fragaria plant having one desired characteristic (or trait) with another polyploid Fragaria plant, such characteristic will be expressed in substantially all of its progeny (i.e. within the bounds of biological certainty, which is, in general in more than 95% of its progeny).

Figure 1:
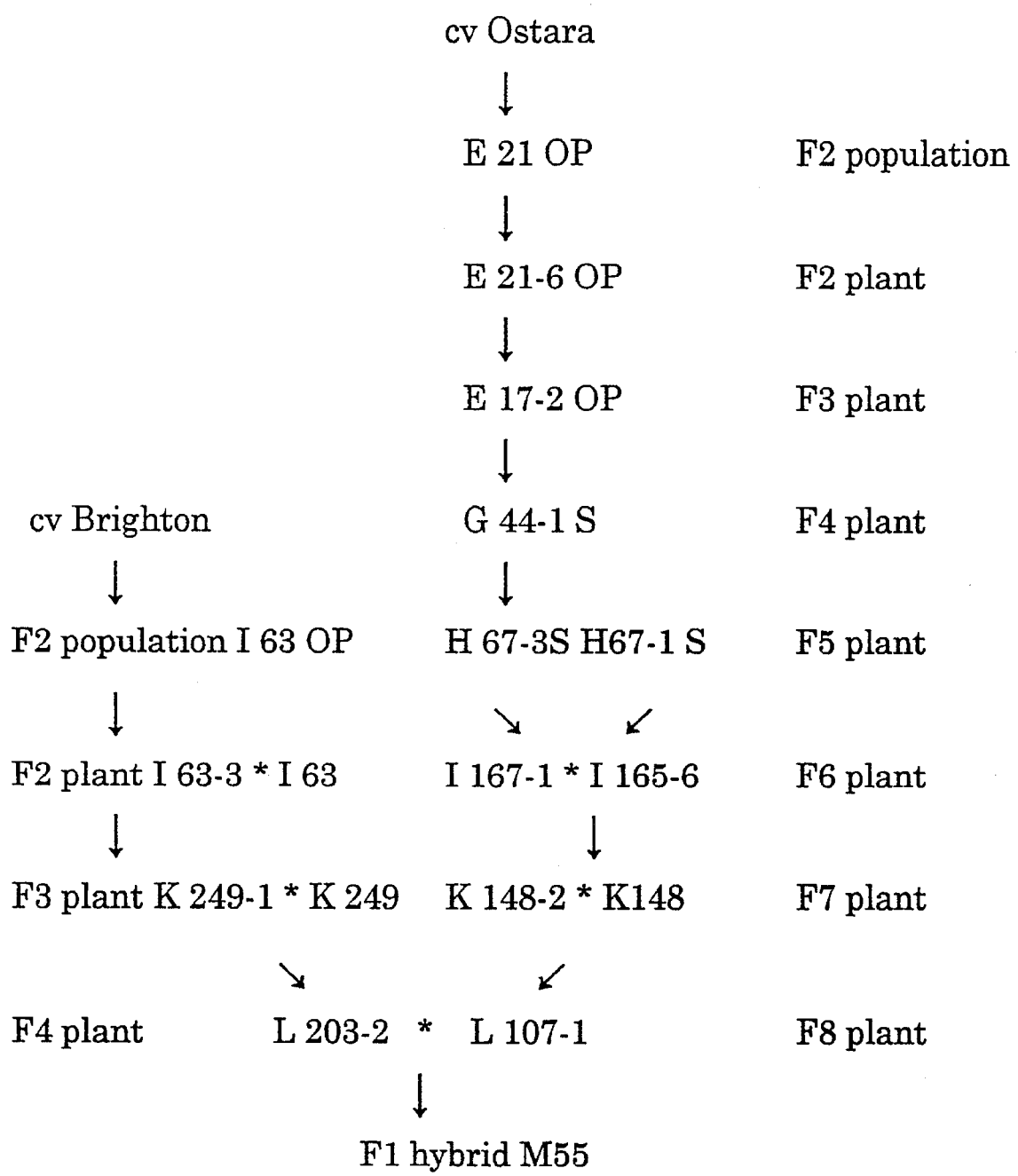
FIG. 1—outlines the development of two day neutral (DN) parent lines in the production of Fragaria F1 hybrid plants displaying reduced number of runners and a fruit productivity for each plant in the first year.

In all four figures, the plant on the right hand side of each cross is the male plant.

DETAILED DESCRIPTION

According to the present invention there are provided cultivated polyploid Fragaria plants propagatable from seed wherein substantially each plant is capable of a fruit productivity within its first year.

'Polyploid' means that the Fragaria plants are not diploid. They may display any ploidy level which may be found in the family Fragaria from triploidy through to octoploidy, nonaploidy, decaploidy or higher ploidy levels. Preferably, such Fragaria plants are octoploid.

The term 'plants' refers to whole plants and parts thereof, including seed, berries, plant tissue and cells thereof.

The Fragaria plant may be selected from the group comprising *F. x ananassa, F.chiloensis, F. virginiana, F. moschata* and the like. A list of commercially important vegetatively propagated cultivars representative of various Fragaria species is provided in Fruit Varieties Journal 42(3):102–108(1988) herein incorporated by reference, and the species so represented by the cultivan described therein are also included in the definition of Fragaria plants propagatable from seed of the invention. A preferred Fragaria species is that of *F. x ananassa*. Preferably, the *F. x ananassa* is octoploid.

"Substantially each plant is capable of a fruit productivity in its first year" means that substantially each plant is capable of a fruit productivity in its first season after sowing or that the plant displays a fruit productivity within a particular season during its first year. Naturally, such a fruit productivity will be dependent on normal conditions required for pollination such as for example their being enough pollinating insects around in a particular season.

'Substantially each plant' means more than 90%, particularly more than 95%, most preferably at least 99% of the plants.

In addition to their capability to produce fruit within its first year from sowing, the plants of the invention preferably display similarity in one or more further commercially valuable traits. Typical examples of desirable commercially valuable traits are berry shape, berry size, fruit productivity, fruit taste, seed or achene coat permeability, daylength neutrality, number of runners per plant. A particularly preferred characteristic of the plants of the invention is daylength neutrality (i.e. that they can be grown year round, independent from the production area). The term daylength neutrality means that flower buds are inducible and yield fruit substantially independent of daylength, and irrespective of that be natural diurnal daylight, artificial light or a combination thereof. According to another particularly preferred characteristic the plants of the invention produce no or very few runners as compared to commercially available vegetatively propagated types. Typically, preferred plants of the invention will have less than 5 runners per plant. Plants which do not produce runners are especially preferred. Plants with a reduced number of runners produce more fruit per plant.

The mature berries of plants of the invention for fresh consumption will preferably have an average diameter of at least 25 mm at its widest point.

The plants of the invention most preferably display a general uniformity in appearance or similarity in plant habit, i.e. a similarity acceptable to the commercial strawberry grower. The plants may accordingly display tolerable differences in plant habit in the sense that such differences would not adversely influence the purchasing decision of customers to buy from the grower. For instance a difference in leaf shape in 5% of the plants may not constitute a commercially unacceptable difference whereas a difference in berry shape in the same percentage of plants could.

Particularly perferred polyploid Fragaria plants according to the invention are in F1 hybrid form, they are preferably octoploids, more preferably octoploid *F. x ananassa* plants. The invention also provides parent lines of such F1 hybrid plants according to the invention and later generations derived from F1 hybrid plants according to the invention.

For the purposes of the present invention a polyploid F1 hybrid plant is one which is a product of a cross between parent lines which show substantial uniformity in inheritance of desired characteristics after several generations of inbreeding. The term substantial uniformity in inheritance means more than 90%, particularly more than 95%, most preferably at least 99% of uniformity in inheritance. Typically, the choice in parent line involves inter alia an assessment on the combining ability of the selected parent lines. Such an assessment can be made when the parent lines display a predictable expression of a desired characteristic or a combination of desired characteristics. Such polyploid F1 hybrids display phenotypically homogeneous expression of commercially desirable characteristics.

Such plants typically display similarity in plant habit to such an extent that the grower may be prepared to overlook those irregularities in plant habit which would not affect the commercial viability of the product.

The invention also provides seeds giving rise to plants according to the invention and strawberry fruits or berries from plants according to the invention.

Also encompassed within the ambit of the present invention are polyploid Fragaria plants which may be produced from seed of F1 hybrid Fragaria plants as described above. Seed of F1 hybrid Fragaria plants may give rise to progeny in the F2 or later generations which are seed propagatable and capable of producing fruit in their first season and in which the expression of desired characteristics of the F1 hybrid generation may be seen in such populations. The progeny, F2 and further generations of Fragaria plants derived from the F1 hybrid will show progressive segregation with respect to the expression of desired characteristics of the F1 hybrid, but may still fall within the scope of the invention.

The fruits or berries of plants of the invention can be destined for any sort of consumption such as fresh eating as well as for processed forms of the fruit or berry such as in jams, confitures, fruit drinks, canned goods, liqueurs, cordials and the like.

The polyploid Fragaria plants according to the invention am capable of being propagated from seed in commercial quantities. Advantages of producing seed for sale in commercial quantities for the large scale production of strawberry plants as opposed to providing plants which are vegetatively propagated are that seed generally gives rise to disease-free material, production costs may be reduced, and delivery and growing may be better planned. Where delivery to tropical countries is envisaged the provision of disease-free strawberry seeds would be particularly advantageous.

In order to attain polyploid Fragaria plants and polyploid Fragaria F1 hybrid plants of the invention a breeding protocol is established wherein inbreeding depression is controlled and wherein the object is to obtain F1 hybrids, phenotypic uniformity in parent lines is maximised.

The present invention accordingly provides a method of producing seed propagatable polyploid Fragaria plants wherein substantially each plant is capable of a fruit productivity within its first year which comprises selecting seedlings displaying the characteristic of interest from a population of seedlings and inbreeding such seedlings until the desired characteristic is stably inherited and capable of being reliably reproduced in each further generation. The number of inbreeding steps can be any number, however the number of steps generally involves about 4 steps, and can involve between 4 and 10 steps or more.

Preferably, the method of the invention makes use of full sib family or half-sib family selection steps. Such selection steps allow it to circumvent the problems involved with inbreeding depression typical for polyploid Fragaria plants as described in the art.

The selection steps will conveniently involve selection for further traits of commercial value, e.g. one or more of the traits outlined above, particularly daylength neutrality and a low number (or absence) of runners.

To increase the germination frequency of the seeds, it may be advantageous to employ a seed enhancement step in one or more of the selection steps. Thus obtained plants may be crossed to form hybrids. If the parent lines satisfy the criterion of similarity in plant habit required for commercial purposes, they may be employed as parent lines for the production of F1 hybrid plants according to the invention.

The production of the hybrid plants according to the invention typically involves the steps of i) crossing of parent lines;

ii) harvesting the seeds of the said cross;

iii) sowing the seeds; and iv) optionally employing a seed enhancement step at any suitable point prior to step iii).

Fragaria seeds are true fruits or achenes which have impermeable, hard coats and depending on the permeability of the coat and/or seed dormancy, the seeds can take varying times to germinate. It is possible to select within the breeding program for plants giving rise to seeds having relatively more permeable seed coats and/or no seed dormancy and correspondingly fast germination times and therefore naturally high germination frequencies.

Alternatively, seeds of plants utilised within the breeding program, as well as final product seeds may be subjected to a seed enhancement step at any suitable time. The seed enhancement step typically includes a treatment which weakens or increases the permeability of the seed coat without substantially interfering with the viability of the seed, either through physical means, e.g. scarification, or through chemical means, such as through the application of enzymes capable of acting on the seed coat, or through the application of mild bleaching agents (eg 1% solution of sodium hypochlorite for 15 minutes) and the like. The application of a seed enhancement step, if required, can improve the overall germination frequency of seed from Fragaria plants of interest to at least 85% depending on requirement. For example, for seeds from a Fragaria line selected for inter alia permeable seed coats (i.e. having a naturally high germination frequency) there may be no need to employ a seed enhancement step. However, in the case where the seed does not have a naturally high germination frequency, a seed enhancement step may be required. Thus in a preferment of the invention there are provided polyploid Fragaria plants of the invention which produce seeds having a germination frequency of at least 85%.

Once the desired characteristic or characteristics are sufficiently stably integrated into the parent lines of interest they may then be crossed. The product of such a cross is regarded as an F1 hybrid in accordance with the definition provided herein. The F1 hybrids propagatable from seed display a stable plant habit from a commercial point of view as hereinbefore described.

In a preferred embodiment of the invention the hybrids of the invention are obtained employing a male sterile parent line.

Such male sterile parent line can be obtained by breeding a parent line employing the selection steps and optionally the seed enhancement step specified hereinabove and then crossing such parent line with a male sterility donor plant to obtain a male sterile plant and then backcrossing the said male sterile plant with the said parent line.

In the case where the population of such plants is made up of a mixture of male sterile and male fertile plants there should also be a sufficient number of male fertile plants present such that pollination may proceed. Should the Fragaria plants be grown in a greenhouse and induced to flower or fruit in any season, for example winter, normal conditions for pollination may include any conventional pollinating procedures such as hand-pollination, the introduction of a colony of pollinating insects into the greenhouse and the like.

The introduction of a back-crossing element into the breeding methods outlined above introduces the characteristic of male sterility into a parent line and reduces or eliminates the requirement to hand emasculate the fully fertile plants obtained in at least one of the parent lines used in the production of seed. The number of back crosses required can be any number, however it is generally found that at least three backcrosses may be required. The F1 hybrid plants resulting from sowing of the F1 seeds according to the invention are a mixture of fully fertile and male sterile plants since segregation with respect to male sterility occurs, however, in respect of the inheritance and expression of other desired characteristics the resultant plants conform with the description of commercial acceptability.

There now follows a general description of how to obtain a polyploid F1 hybrid Fragaria plant of the invention wherein the trait of male sterility is utilised in the breeding process.

Strawberry plants propagated from runners are selfed to provide an F2 population. These F2 populations display genotypic segregation. Plants displaying certain desired characteristics are selected in pairs from the F2 generation and crossed to provide an F3 generation, called a full sibling family (full sib family). The process of crossing full sib selections is repeated for subsequent generations until a sufficiently homogeneous parental line with respect to the expression of commercially desirable characteristics is able to be maintained. Members of such a full sib family parental line may then be cloned using conventional techniques such as tissue culture techniques or vegetative propagation techniques. Alternatively, such a full sib parental line may be permitted to set seed. In a variant on the above, use may be made of half-sib family selection lines. A half-sib family is one wherein selected plants of one line are pollinated with a pollen mixture obtained from these plants themselves or from plants of two or more further lines. The progeny (i.e. the seeds or plants) of a separate harvested plant is designated as a half-sib family. Thus, the female parent plant is known but the male parent plant is not. The half-sib lines may be treated in the same manner as the full sib lines with respect to selection and crossing until a sufficiently homogeneous parental line with respect to the expression of commercially desirable characteristics is able to be maintained. Members of such half-sib family parental lines may then be cloned using conventional techniques. Alternatively, the half-sib family parental line may be permitted to seed.

Using either full sib family selection or half-sib family selection as described above, or other conventional breeding methods such as recurrent selection or mass selection, parental lines displaying commercially desirable characteristics may be treated as described hereinbelow.

One parental line displaying commercially desirable characteristics may then be back-crossed several times with a male sterility donor plant in order to introduce male sterility into the said parental line. Once male sterility is introduced into this parental line by back-crossing it is crossed with a fully fertile parent line carrying a desirable characteristics. (In the alternative, and as alluded to above, the characteristic of male sterility can also be introduced into a parent line by simply selecting a plant displaying the characteristic of male sterility and introducing that characteristic into a prospective parent line utilising conventional procedures employed in breeding programs such as recurrent selection and mass selection). The product of such a cross is F1 hybrid seed which can give rise to F1 hybrid plants.

According to a further preferred embodiment, the plants of the invention are cloned, employing conventional tissue culture techniques and growth medium.

This cloning step facilitates large scale production of the plants (including plant parts, tissue, fruit and seed thereof) of the invention.

The use of tissue culture techniques is particularly indicated for the mass production of one or both parental lines for hybrid production.

Cloning here refers to the multiplication of tissue of plants according to the invention and subsequent multiplication of that to produce large numbers of plants with the same genotype. Cloned plants may be crossed either with plants obtained through conventional inbreeding and crossing techniques or with other suitably cloned plants. In a preferment, cloned parent plants may be crossed with other cloned parent plants and the seeds of such crosses harvested. Alternatively, tissue capable of being cloned in tissue culture may be taken from plants of the invention and used to clone such plants per se. Such tissue derived material may be grown to seedling stage and sold to growers in commercial quantities. 'Tissue' may refer to individual cells, organs of plants such as roots, shoots, leaves or pieces of organs, seedlings and the like.

F1 hybrid seeds M8 (Example 2 hereinafter) and M55 (Example 1 herinafter) have been deposited 9th Nov. 1992 with the NCIMB, Aberdeen and allocated deposit numbers NCIMB 40527 and NCIMB 40528 respectively.

The invention will now be further described with reference to the following examples. It is to be understood that the examples are not intended to limit the scope of the invention in any way.

EXAMPLE 1

Production of F1 hybrid octoploid Fragaria plant displaying reduced numbers of runners, and fruit production per plant utilising two day neutral lines.

Reference is made to FIG. 1 hereinafter.

A vegetatively propagated octoploid Fragaria variety, cv Ostara (CPRO, Wageningen), displaying inter alia day neutrality and soft fruit is selected and seed is harvested therefrom. The seed gives an F2 population designated with the in-house number, E 21 OP (where OP stands for open pollinated). A plant is selected from the F2 population (E21-6) open pollinated and seed harvested therefrom. The seed gives an F3 population, designated F17. A plant is selected from this F3 population and designated F 17-2, open pollinated and seed harvested therefrom. The seed gives an F4 population designated G 44. A plant is selected from this F4 population and designated G 44-1. G 44-1 is self pollinated (S) and seeds harvested therefrom. Seeds of G 44-1 are sown and seedlings designated H 67. Two plants designated H 67-3 and H 67-1 m selected, self pollinated respectively and seeds are harvested therefrom. Seeds from H 67-3 S and H 67-1 S are sown separately (i.e. without mixing the two seed populations) and populations of seedlings obtained designated I 167 and I 165. Plants (I 167-1 and I 165-6) from the two sister lines are crossed to restore plant vigour. Seeds harvested from this cross are sown and are given the field designation K 148. Half-sibs are created by taking five female parent plants from K 148 and pollinating them with a mixture of pollen from the same five parent plants thereby creating a subpopulation of K 148. Plants are harvested separately from K 148. Out of the half-sibling population the progeny of one of the selected plants (K 148-2) is designated L 107, and a plant is selected from this population and given designation L 107-1. This plant is the male parent plant i.e. the F8 inbred generation from cv Ostara. These plants display inter alia day neutrality and reduced numbers of runners.

Female parent lines are created from seeds harvested from a vegetatively propagated octoploid Fragaria variety, cv Brighton (University of California), in the open field and plants derived therefrom are designated I 63 OP (F2). Half-sib families of I 63 are created using a similar procedure to that used in obtaining the male parent line. Mixing of seeds of the half-sib families is avoided. The half-sib families are sown and one of them designated K 249. Half-sib families of K 249 are created using a similar procedure to that described in obtaining the male parent line above. Mixing of seeds of the half-sib families is avoided. The half-sib families are sown and the progeny of one of the selected plants (K 249-1) is designated L 203. A plant is selected from this L 203 population and designated L 203-2. This plant is the female parent plant (i.e. the F4 inbred generation from cultivar Brighton) and displays the characteristics inter alia of medium day neutrality, reduced numbers of runners, and fruit productivity per plant within its first year.

The two parent lines are crossed to create F1 hybrid plants which are designated M 55. These octoploid Fragaria plants display homogeneous fruit production, fruit size and shape, reduced numbers of runners, day neutrality, and a fruit productivity within their first year.

EXAMPLE 2

Production of an F1 hybrid octoploid Fragaria plant displaying fruit production in its first year utilising a day neutral line and a short day line.

Figure 2:
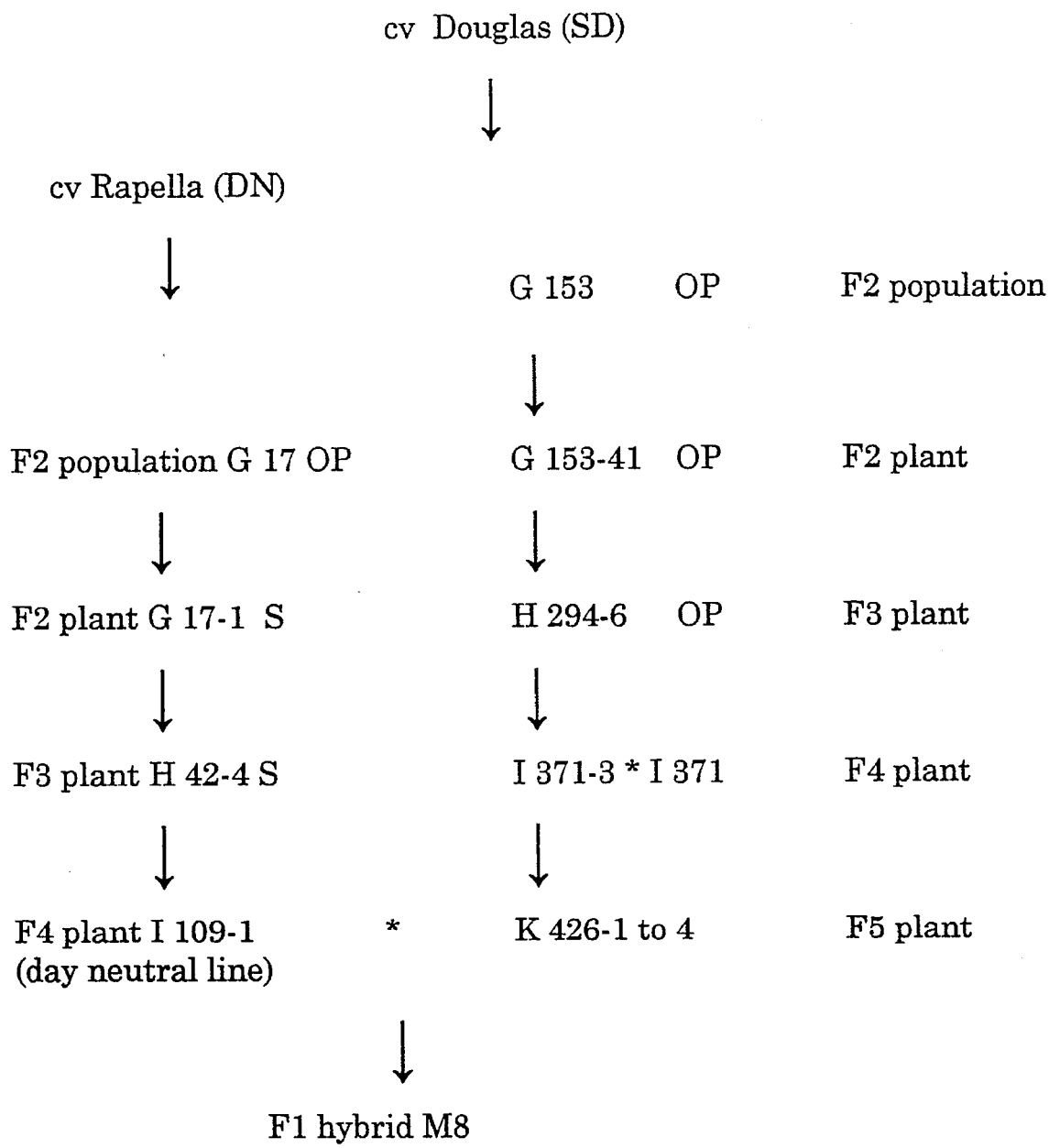
FIG. 2—outlines the development of day neutral (DN) and short day (SD) parent lines in the production of Fragaria F1 hybrid plants displaying a fruit productivity for substantially each plant in its first year.

Reference is made to FIG. 2 hereinafter.

Seeds from cv Douglas (University of California) a short day vegetatively propagated octoploid Fragaria variety, are sown to provide a population designated G 153 OP (F2). A plant is selected from this population and designated G 153-41, open pollinated, and the seed harvested therefrom and sown to provide a population designated H 294. A plant is selected from this population and designated H 294-6, open pollinated, and the seed harvested therefrom and sown under designated number I 371. Out of I 371, half-sib families are created using procedures as outlined in example 1. One of these half-sib families (I 371-3) is sown under designation K 426. Out of K 426 four plants are selected and the pollen of these plants is mixed for crossing with I 109-1 to test for combining ability. Combining ability is assessed via observing the inheritance of characteristics of a line in combination with other lines.

Seeds from a vegetatively propagated, day neutral octoploid Fragaria variety Rapella (CPRO, Wageningen) are sown and given the designated population number G 17 OP. A plant is selected from this population and designated G 17-1 and self pollinated. The seeds of G 17-1 are sown, grown and the resultant population designated H 42. A plant from this population is selected and given the designation H 42-4 and self pollinated. The seeds of H 42-4 are sown, grown, and the resulting population given the designation I 109. A plant is selected from this population and designated I 109-1. This plant is a female parent plant which displays inter alia day neutrality.

I 109-1 and pollen from the four plants from K 426 are crossed. This results in the octoploid Fragaria F1 hybrid plant M 8. These plants display inter alia uniform vigorous plant habit, high fruit yield, and fruit production per plant in their first year.

EXAMPLE 3

Production of an F1 hybrid octoploid Fragaria plant displaying fruit production in all plants demonstrating the use of the trait of male sterility in the breeding scheme.

Figure 3:
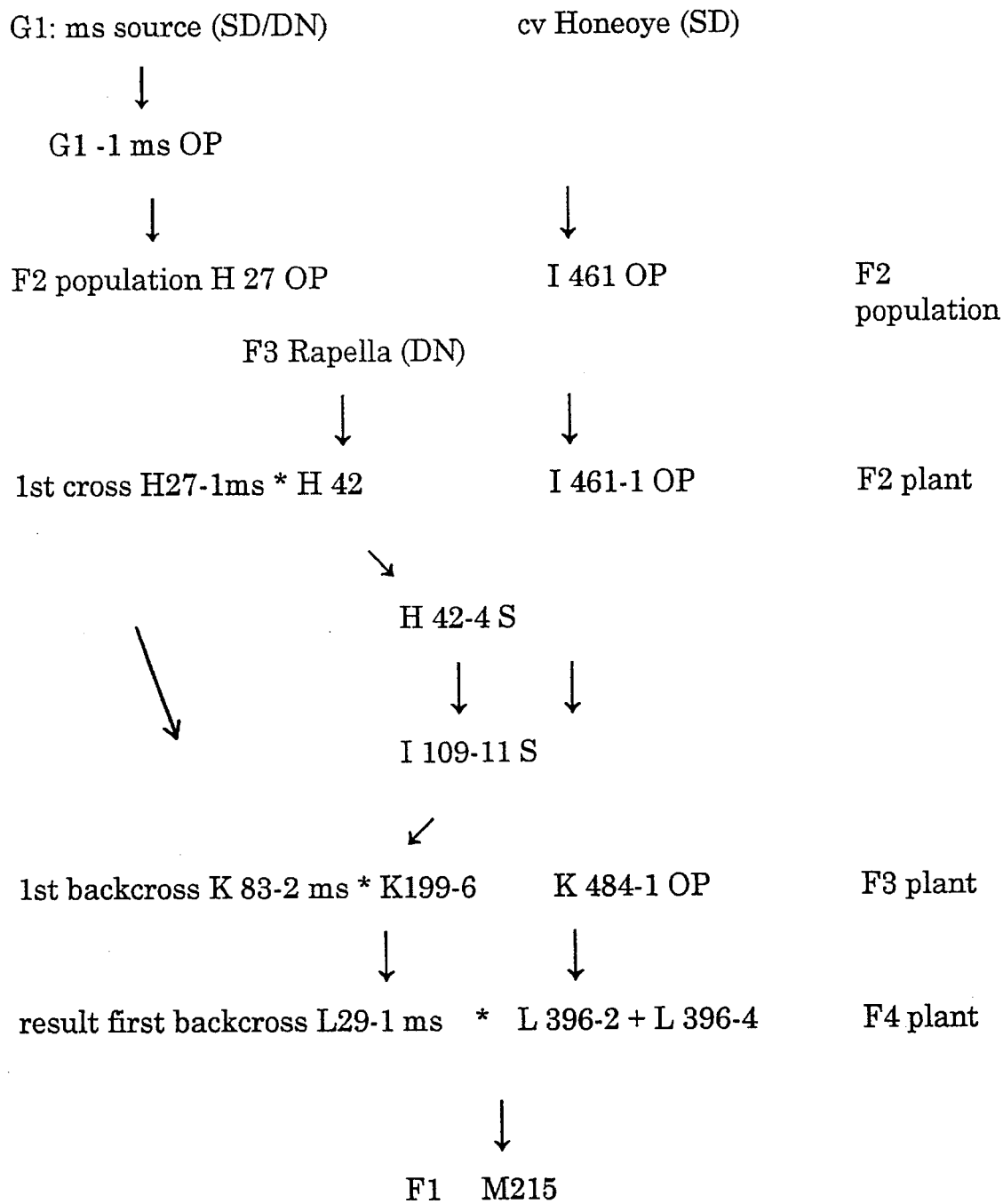
FIG. 3—outlines the initial steps in the development of male sterile (ms) and fertile (f) parent lines in the production of Fragaria F1 hybrid plants displaying uniformity in plant characteristics but segregating with respect to the trait of male sterility.

Reference is made to FIG. 3 hereinafter.

Seeds from a short day vegetatively propagated octoploid Fragaria variety, cv Honeoye (Cornell University, Geneva Expt. Station, NY State) are sown and the population of seedlings given the designation I 461 OP. A plant is selected from this population, I 461-1, and seeds produced via open pollination are then sown. From the population of seedlings, K 484, a plant is selected (K484-1), open pollinated and seeds therefrom are sown, producing population, L 396. Two plants (L396-2 and L 396-4) are selected to provide a pollen mixture which is used to fertilise the female parent plant, L 29-1 ms.

Seeds from a male sterile source, an octoploid experimental Fragaria plant displaying male sterility, are designated G 1. (Seeds from any Fragaria plant displaying the characteristic of male sterility may be selected as a male sterility source. An example of a commercially available variety which may be used as a male sterile source is cv Pandora, East Mailing Experimental Research Station). G 1 seeds are sown, grown, and a plant displaying male sterility is selected, G 1-1 ms. Seeds are produced via open pollination and harvested from G 1-1 ms and sown providing a plant population designated H 27 OP. A plant displaying male sterility is selected from this population, (H 27-1 ms ), and is crossed with a pollen mixture from a group (H 42) of ten (10) plants selected from an F3 Rapella day neutral variety population created via general selection procedures such as those employed for other lines as described above (e.g. F4 plant I 109-1, FIG. 2), providing a population of plants (K 83) from which K 83-2 ms is selected and backcrossed with K 199-6 an F5 Rapella plant. From the resulting population, designated L 29 a plant displaying male sterility is selected (L 29-1 ms ) and crossed using pollen of the plants L 396-2 and L 396-4 which results in an F1 hybrid, M 215. All plants of this F1 octoploid hybrid display a fruit productivity and segregate 50%:50% with respect to male sterility.

EXAMPLE 4

Production of F1 hybrid octoploid Fragaria plants displaying uniformity in plant characteristics and segregating 50%/50% with respect to male sterility utilising short day (SD) and day length neutral (DN) lines.

Figure 4:
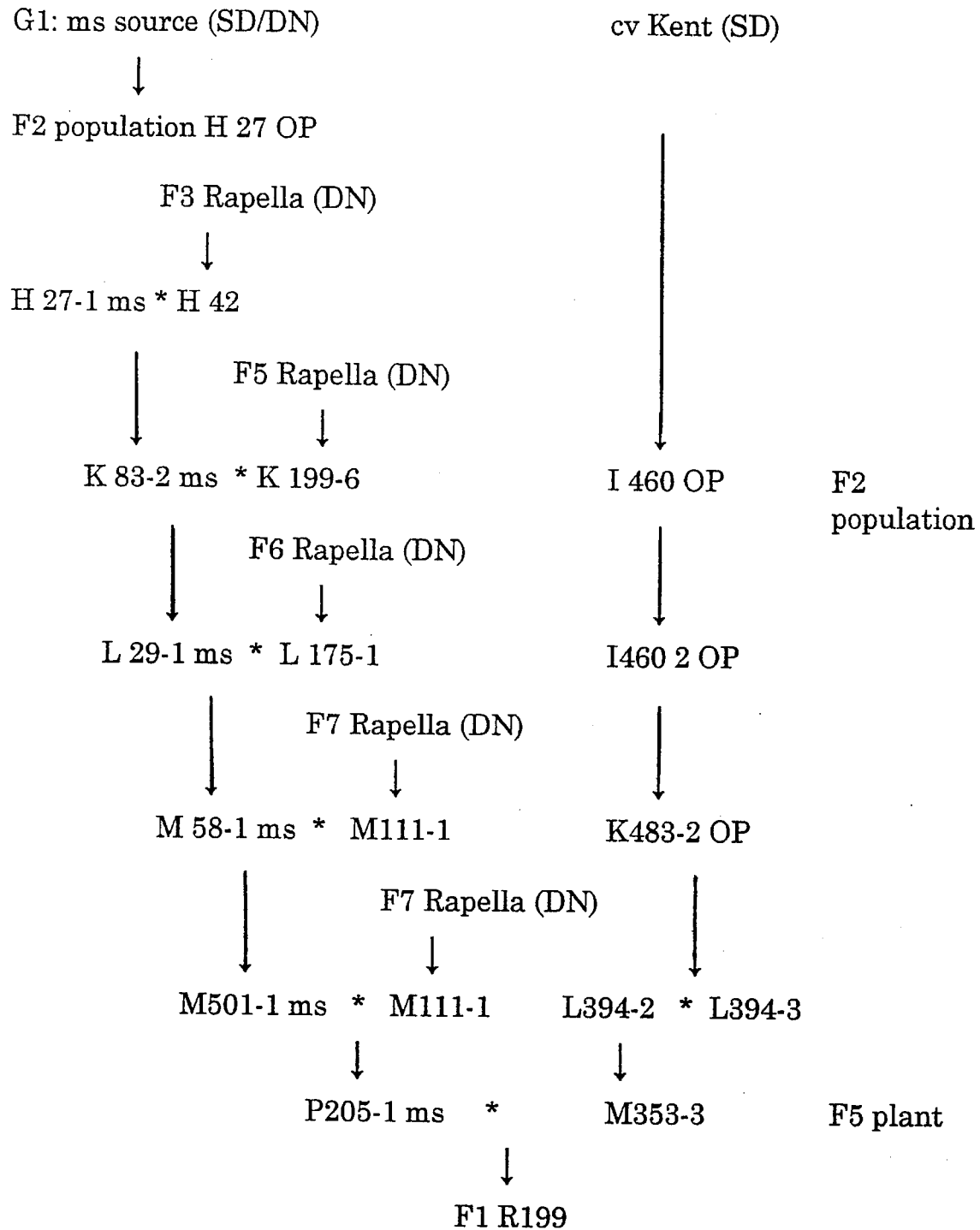
FIG. 4—outlines the full development of male sterile (ms) and fertile (f) parent lines in the production of Fragaria F 1 hybrid plants displaying uniformity in plant characteristics but segregating 50/50% with respect to the trait of male sterility.

Reference is made to FIGS. 2, 3 and 4 hereinafter.

Seeds from a short day (SD) vegetatively propagated octoploid Fragaria variety, cv Kent (Agricultural Research station, Kentville, Nova Scotia, Canada) are sown and the population of seedlings (F2 population) given the designation I 460 OP (where OP stands for open pollinated). A plant is selected from this population, 1 460-2, and seeds produced via open pollination are then sown. From the population of seedlings, K 483, a plant is selected (K 483-2), open pollinated and seeds therefrom are sown, producing population L 394. Two plants, L 394-2 and L 394-3, are selected from the L 394 population and crossed to provide a full sib family designated M 353. F5 Plant, M 353-3, is selected as the male parent of the F1 hybrid R 199.

Seeds from a male sterile some, an experimental octoploid Fragaria plant displaying male sterility, are designated G 1. (Seeds from any Fragaria plant displaying the characteristic of male sterility may be selected as a male sterility some. An example of a commercially available variety which may be used as a male sterile source is cv Pandora, East Malling Experimental Research Station). G 1 seeds are sown and a plant displaying male sterility is selected (G 1-1 ms). Seeds are produced via open pollination and harvested from G 1-1 ms and sown. The resultant population of plants is designated H 27 OP. A plant displaying male sterility is selected from this population, (H 27-1 ms) and is crossed with a pollen mixture from a group (H 42) of ten (10) plants selected from an F3 Rapella day neutral variety population created via general selection procedures such as those employed for other lines as described above (e.g. F4 plant I 109-1, Breeding Scheme 2), providing a population of plants (K 83) from which K 83-2 ms is selected and backcrossed with K 199-6 an F5 Rapella plant. The population resulting from this first backcross is designated L 29. Out of L 29, a male sterile plant L 29-1 ms is selected and backcrossed with an L 175-1 plant from an F6 Rapella population (L 175). The result of this backcross is designated M 58. Out of this M 58 population a male sterile plant is selected, M 58-1 ms, and backcrossed to M 111-1, an F7 plant selected out of an F7 Rapella population. The population resulting from this backcross is designated M 501. Out of the M 501 population a male sterile plant is selected, M 501-1 ms, and backcrossed with an M 111-1 plant yielding a male sterile population, P 205, from which a male sterile plant is selected for crossing with M 353-3. P 205-1 ms is the fourth backcross to Rapella.

Plants P 205-1 ms and M 353-3 are crossed, resulting in octoploid F1 hybrid R 199 displaying phenotypical uniformity at least with respect to fruit productivity in its first year, day neutrality, and 50%:50% segregation for male sterility.

EXAMPLE 5

Effect of Seed Enhancement Treatment on octoploid *Fragaria x ananassa* F1 hybrid seed 3×1 lots of 6 gms of octoploid *Fragaria x ananassa* F1 hybrid seed (inhouse designations K1, K2, and K3) are placed in 300 mls of a 7% by volume solution of sodium hypochlorite at an initial temperature of 20° C., for time intervals of 15, 30, and 45 minutes. Controls are placed in 300 mls of water at 20° C. over the same time intervals; all other experimental parameters being the same as for test samples. The temperature of the test samples starts at 20° C. rising to 23° C. during the test. After each time interval the seeds are removed from the solution, placed in a nylon mesh bag and washed in 10 liters of water for 1 minute. The washing procedure is repeated a further two times. After washing the seeds are centrifuged for 1 minute at 1000g. Seeds are further dried in an airstream (about 40 m/minute) for a period of up to 24 hours. Germination is tested on samples of 200 seeds from each seed lot by sowing treated seeds and controls on top of paper in the light at 25° C. and germination monitored daily for 28 days by counting the number of protruding radicles. Total germination is determined at 28 days. 50% total germination ($T_{50}$) and spread is determined following the method as outlined by Orchard T. J. (1977) Seed Sci. & Technol., 5, 61–69.

Results are shown in Table 1.

TABLE 1

| | Treatment (Sodium chlorite) (Days) | T50 Day 14 | Spread Day 14 | % Germ Day 28 | % Germ Day 28 |
|---|---|---|---|---|---|
| Seedlot 1 (K1) | Control (water) | 12.0 | 4.8 | 59 | 88 |
| | hypo 7% 15 min | 10.5 | 3.4 | 82 | 97 |
| | hypo 7% 30 min | 7.2 | 2.8 | 97 | 100 |
| | hypo 7% 45 min | 6.6 | 2.1 | 98 | 99 |
| Seedlot 2 (K2) | Control (water) | 13.2 | 5.1 | 58 | 94 |
| | hypo 7% 15 min | 10.6 | 5.4 | 81 | 99 |
| | hypo 7% 30 nun | 8.1 | 3.3 | 91 | 97 |
| | hypo 7% 45 min | — | — | — | — |
| Seedlot 3 (K3) | Control (water) | 12.2 | 5.2 | 67 | 98 |
| | hypo 7% 15 min | 10.4 | 3.8 | 82 | 98 |
| | hypo 7% 30 min | 7.1 | 2.2 | 97 | 98 |
| | hypo 7% 45 min | 7.1 | 2.2 | 100 | 100 |

1) k87.1 × k407.1 F1 hybrid K1
2) k87.1 × k407.1 F1 hybrid K2
3) k148.2 × k407.1 F1 hybrid K3
— not done

EXAMPLE 6

Cloning of octoploid Fragaria plants utilising Tissue Culture techniques

Explant material comprising stem material containing meristem material is cut from runner tips of K 148-2 and surface sterilised by firstly dipping (no more than 5 secs) in a 70% solution of ethanol. The material is then placed in a 1.5% by volume solution of sodium hypochlorite (30 ml) (Glorix, Fenix BV Zwolle, NL) and surface sterilised for 15 minutes on a rotary shaker set at 200 rpm at room temperature. The explant material is then rinsed in 3 volumes (3×30 ml) of sterile physiological salt solution (8.5 g/l) and meristem tissue excised from the stem thereafter. Metistem tissue is placed in culture tubes (2 cm diameter) containing 16.7 ml initiation culture medium per tube. The initiation medium contains: macro-elements as described by Knop W [(1865) Landw. Vers. Stn. 7: 93–107] supplemented with:

10 mg/l $FeSO_4.7 H_2O$ and 10 mg/l $Na_2EDTA$ micro-elements and organic elements as described by Murashige T. & Skoog F [(1962) Physiol. Plant. 15:473–497]

1.2 mg/l KIBA (Indole-3-butyric acid- Sigma)

0.1 mg/l BA ($N^6$-Benzyl adenine (Fluka AG)

44 g/l glucose monohydrate 7 g/l agar (Lab M) (Amersham, UK)

pH 5.6

31 meristems are placed in the dark for 7 days then transferred to light conditions of (16 hrs light 3000 lux/8 hrs dark). Temperature is maintained in the range of from 22°–24° C. After 6 weeks shoots formed are placed in glass jars having lids with interrupted inner rims (to allow gaseous exchange to take place), on 62.5 ml multiplication medium comprising the same elements as the initiation medium except for plant hormone concentration being KIBA 1.2 mg/l and BA 1.0 mg/l. Temperature and light conditions are the same as for the initiating cultures; multiplication period of 7 weeks. At the end of the multiplication period 150 shoots are collected and transferred to roofing medium. (In order to obtain more shoots for rooting from the multiplication step shoots may can be sliced into more pieces depending on how many plants are required, and then placed on multiplication medium). The rooting medium is similar to the multiplication medium except that BA is excluded from it. The rooting period is 6 weeks; all other parameters are the same as for the multiplication step. After the rooting period, rooted shoots are rinsed carefully in luke warm water and transferred to potting soil 3 (commercially available from Jongkind Grond BV Aalsmeer, NL) and permitted to grow into plantlets under glass jars at a high relative humidity (95%). Hardening of the plantlets is effected by gradual reduction of the relative humidity to about (70) over a period of 2 weeks. Plantlets are then transferred to the greenhouse.

Plantlets of K 148-2 are of good quality and display a survival rate of 99% in the greenhouse

We claim:

1. A method of producing F1 polyploid Fragaria plants propagatable by seed comprising,
   a) selecting and crossing parental lines that, when crossed, will reliably produce F1 seedlings that bear fruit in the first season of growth;
   b) harvesting the seeds of said cross;
   c) sowing said seeds; and
   d) allowing said seeds to grow to produce F1 polyploid Fragaria seedlings
   wherein at least 90% of the plants produced from said seed produces fruit within their first season after sowing.

2. A method according to claim 1 further comprising employing a seed enhancement step prior to sowing the seeds.

3. A method according to claim 1 wherein one of the parent lines is a male sterile parent.

4. A method according to claim 1 further comprising selecting seedlings having a trait selected from the list consisting of berry shape, berry size, fruit productivity, fruit taste, seed or achene coat permeable, daylength neutrality, and number of runners per plant from the seed step d) and inbreeding the seedling until the trait is stably inherited and capable of being reliably reproduced in further generations.

5. A method according to claim 4 wherein the number of inbreeding steps is between 4 and 10.

6. A method according to claim 1 wherein said parental lines of step a) show substantially uniformity of inheritance for one or more characteristics selected from the group consisting of berry shape, berry size, fruit productivity, fruit taste, seed or achene coat permeability, daylength neutrality, and number of runners per plant.

7. The F1 polyploid Fragaria plants produced according to the method of claim 1.

8. The F1 polyploid Fragaria plants produced according to claim 7 wherein said plants are day neutral plants.

9. The F1 polyploid Fragaria plants produced according to claim 7 wherein said plants are octoploid.

10. The F1 polyploid Fragaria plant according to claim 9 wherein said plants are *F. x ananassa*.

11. The seed of the Fragaria plants produced according to the method of claim 7.

12. The strawberry fruits of the Fragaria plants produced according to the method of claim 7.

13. A method of producing F1 hybrid Fragaria seeds of polyploid Fragaria plants comprising,
   2) selecting and crossing one parental line or clone from the parental line with a second parental line or a clone from the second parental line that, when crossed, will reliably produce F1 seedlings that bear fruit in the first season of growth; and wherein both parental lines or clones thereof show substantial uniformity in inheritance of characteristics selected from the group consisting of berry shape, berry size, fruit productivity, fruit taste, seed or achene coat permeability, daylength neutrality, and number of runners per plant; and
   b) harvesting the seed of said cross;
   wherein at least 90% of said seed give rise to Fragaria plants that produce fruit within the first growing season from sowing.

14. The hybrid Fragaria plants produced according to the method of claim 13.

15. The strawberry fruits of the hybrid Fragaria plants of claim 14.

16. The hybrid Fragaria plants produced according to claim 13 wherein said plants are octoploid.

17. The hybrid Fragaria plants produced according to claim 13 wherein said plants are day neutral plants.

18. The method according to claim 13 wherein one of the parental lines is male sterile.

19. The seed of the Fragaria plant produced accordingly to the method of claim 14.

* * * * *